US006268357B1

(12) United States Patent
Orvig et al.

(10) Patent No.: US 6,268,357 B1
(45) Date of Patent: Jul. 31, 2001

(54) ORGANIC VANADIUM (III) COMPLEXES AND THEIR USE

(75) Inventors: Chris Orvig; John H. McNeill; Marco Melchior, all of Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/426,414

(22) Filed: Oct. 25, 1999

Related U.S. Application Data

(60) Provisional application No. 60/106,031, filed on Oct. 28, 1998.

(51) Int. Cl.$^7$ .......................... C07F 9/00; A61K 31/555; A61P 31/06; A61P 31/08; A61P 31/10
(52) U.S. Cl. .............................. 514/184; 514/188; 544/4; 544/64; 544/181; 544/225; 546/6; 546/7; 549/3; 549/210
(58) Field of Search ................. 544/4, 64, 181, 544/225; 546/6, 7; 549/3, 210; 514/184, 188

(56) References Cited

U.S. PATENT DOCUMENTS

| | | | |
|---|---|---|---|
| 5,278,154 | * | 1/1994 | Lacoste ..................................... 546/6 |
| 5,300,496 | | 4/1994 | McNeill et al. ...................... 514/186 |
| 5,527,790 | | 6/1996 | McNeill et al. ...................... 514/186 |

FOREIGN PATENT DOCUMENTS

98/49173    11/1998   (WO) .

OTHER PUBLICATIONS

Cooper, Stephen R., et al., "Synthetic, Structural, and Physical Studies of Bis(triethylammonium) Tris(catecholato)vanadate(IV), Potassium Bis(catecholato)oxovanadate(IV), and Potassium Tris(catecholato)vanadate(III)," *J. Am. Chem. Soc.* (1982) vol. 104:5092–5102.

Eaton, S.S., et al., "Intramolecular Rearrangement Reactions of Tris–Chelate Complexes. IV.$^1$ Further Investigation of the Rearrangements of Tris(α–isopropenyl–and α–isopropyl-tropolonato)metal(III,IV) Complexes," *J. Amer. Chem. Soc.* (1973) vol. 95(4):1116–1124.

Evangelou, Angelos, et al., "Comparison of the Therapeutic Effects of Two Vanadium Complexes Administered at Low Doses on Benzo [α] Pyrene–Induced Malignant Tumors in Rats," *Cancer Letters* (1997) vol. 119:221–225.

Lybing, Sigvar, "The Valence of Vanadium in Hemolysates of Bloodcells from *Ascidia Obliqua* Alder," *ARKIv FÖR KEMI* Band 6 nr 21 Communicated Feb. 11, 1953 by John Runnstrom; pp.: 261–269.

Pederson, Raymond A., et al., "Long–Term Effects of Vanadyl Treatment on Streptozocin–Induced Diabetes in Rats," *Diabetes* (Nov. 1989) vol. 38:1390–1395.

Ramanadham, S., et al., "Enhanced In Vivo Sensitivity of Vanadyl–Treated Diabetic Rats to Insulin," *J. Physiol. Pharmacol.* (1990) vol. 68:486–491.

Ramanadham, Sasanka, et al., "Oral Vanadyl Sulfate in Treatment of Diabetes Mellitus in Rats," *Am . J. Physiol.* (1989) (Heart Circ. Physiol. 26):H904–H911.

Ramanadham, Sasanka, et al., "Sustained Prevention of Myocardial and Metabolic Abnormalities in Diabetic Rats Following Withdrawl from Oral Vanadyl Treatment," *Metabolism* (Oct. 1989) vol. 38(10):1022–1028.

Sommer, L. Von, "Ein Selektiver von Vanadium mit Maltol," *Aus dem Institut für analytiscle der J.E. Purkyně–Universität, Brno* (CSSR), (Sep. 1961) pp.: 263–266.

Taylor, Steven W. et al., "Vanadium in Ascidians: Changes in Vanadium Coordination and Oxidation State Upon Cell Lysis," *J. of Inorganic Biochemistry* (1994) vol. 56(2):97–116.

Yuen, Violet G., et al., "Glucose–Lowering Properties of Vanadium compounds: Comparison of Coordination Complexes with Maltol or Kojic Acid as Ligands," *J. of Inorganic Biochemistry* (1997) vol. 68(2):109–116.

Welch, Inorg. Chem 27, 2862, 1988.*

Chauhan, Annali di Chimica 81, 179, 1991.*

* cited by examiner

*Primary Examiner*—Mark L. Berch
(74) *Attorney, Agent, or Firm*—Pamela J. Sherwood; Bozicevic, Field & Francis LLP

(57) ABSTRACT

Organic complexes of vanadium are provided, having the general structure $VL_3$, where V is vanadium(III) and L is a monoprotic bidentate ligand that forms a five-membered, unsaturated vanadium containing ring, having vanadium coordinating oxygen or sulfur ring heteroatoms, and where the vanadium containing ring is fused to a six-membered heterocyclic ring. Preferably L is a hydroxypyrone or a hydroxypyridinone. The complexes have a number of uses, including the treatment of elevated blood glucose and related disorders, treatment of proliferative disorders, etc.

20 Claims, 3 Drawing Sheets

ORGANIC VANADIUM (III) COMPLEXES AND THEIR USE

CROSS-REFERENCE TO RELATED APPLICATIONS

This application claims the benefit of U.S. Provisional application No. 60/106,031, filed Oct. 28, 1998.

BACKGROUND OF THE INVENTION

Vanadium is a trace metal in biological systems and in the environment. Pure anadium is a soft, bright white metal. Like other transition metals, it forms complexes that are often beautifully colored. Vanadium exists in several oxidation states. The most frequently encountered in biological systems are the oxovanadium(V) ion, e.g. vanadate, sodium orthovanadate and sodium metavanadate; and the oxovanadium(IV) ion, e.g. vanadyl and vanadyl sulfate. Other compounds are known in the −1 to +5 oxidation states.

Vanadium(III) oxide is a black refractory substance made by the reduction of $V_2O_5$ with hydrogen or carbon monoxide. $V_2O_3$ is entirely basic in nature, and dissolves in acids to give the V(III) aquo ion or its complexes. The blue aquo ion $[V(H_2O)_6]^{3+}$ can be obtained as above, or by electrolytic or chemical reduction of V(IV) or V(V) solutions. V(III) forms a number of complex ions, mostly anionic, e.g. $[V(CN)_6]^{3-}$, but some are neutral. Coordination complexes of vanadium(III) have been described, including tris (acetylacetonatovanadium(III) (Morgan et al. (1913) *J. Chem. Soc.* 103:78–90); tris(tropolonato)vanadium(III) (Eaton et al. (1973) *J. Am. Chem. Soc.* 94(4):1116–1124); and the trianionic V(III) complex tripotassium tris (catecholato) vanadate(III) (Cooper et al. (1982) *J. Am. Chem. Soc.* 104(19):5092–5102). Sommer (1962) *Z. Anal. Chem.* 185:263–266 disclose the formation of an intensely purple or blue-violet color formed from vanadium(V) with maltol in a medium of 40% $H_3PO_4$ and oxalic, purportedly due to an instable V(III) complex of unknown composition.

Relatively little is known about the biological effect or role of vanadium in the (III) oxidation state. However, sea squirts (ascidians) have a highly unusual requirement for vanadium. The concentration of vanadium in sea squirts is a million times higher than in sea water as a consequence of their ability to concentrate vanadium. Lybing (1953) *Ark. Khem.* 6:261 discloses that vanadium in ascidians is predominantly in the +3 oxidation state, based on a comparison of optical spectra. A more recent evaluation of the changes in vanadium coordination and oxidation state in ascidians may be found in Taylor et al. (1994) *J Inorg Biochem* 56(2):97–116.

More recently, complexes of vanadium(III) with cysteine, and the dipeptide N-(2-mercaptoproprionyl)-glycine were tested in a rat benzopyrene-induced tumor model (Evangelou et al. (1997) *Cancer Letters* 119(2):221–225). It was found that the $[V^{III}(Hcys)_3]$ complex had a significant antitumor effect.

In the (IV) and (V) oxidation state, vanadium has been found to have a number of interesting properties in biological systems. Vanadium was originally recognized for its ability to inhibit membrane $Na^+$-$K^+$-ATPase, but various laboratory studies now document that this element has the capacity to affect the activity of various intracellular enzyme systems, and may modify their physiological functions.

For example, complexes of vanadium(IV) with α-hydroxypyrones and α-hydroxypyridinones have been shown to have an effect in a number of studies. Yuen et al. (1997) *J Inorg Biochem* 68(2):109–116 compare vanadium complexes bis(kojato)oxovanadium(IV) and bis(maltolato) oxovanadium(IV) for their glucose lowering properties. Work by McNeill et al. (see Am. J. Physiol 257: H904–H911 (1989), Metabolism 38: 1022–1028 (1985), Diabetes 38: 1390–1395 (1989) and Can. J. Physiol & Pharmacol. 68: 486491 (1990); U.S. Pat. Nos. 5,527,790; 5,300,496; has shown that vanadyl administered orally as vanadyl sulfate, or as vanadyl maltol complexes, lowers blood glucose and blood lipids in STZ diabetic rats and prevents secondary complications of diabetes such as cataracts and cardiac dysfunction.

The profound effects of vanadium in biological systems makes their synthesis and evaluation a subject of great interest. Novel compounds of vanadium(III) may be explored for their activity in regulating blood glucose, proliferative diseases, bone growth, and other conditions.

SUMMARY OF THE INVENTION

Stable organic complexes of vanadium in the 3+ oxidation state are provided. The complexes have the general structure $VL_3$, where V is vanadium(III) and L is a monoprotic bidentate ligand that forms a five-membered, unsaturated vanadium containing ring, having vanadium coordinating oxygen or sulfur ring heteroatoms, and where the vanadium containing ring is fused to a six-membered heterocyclic ring. Preferably L is a hydroxypyrone or a hydroxypyridinone. Such V(III) complexes may be provided in an isolated form, or in a composition with other agents, e.g. physiologically acceptable carriers. The complexes may also be provided as a hydrate, e.g. $VL_3 \cdot (H_2O)_n$, or as a salt or adduct, e.g. $VL_3 \cdot (Z)_m$ where Z may be HCl, ascorbic acid, bicarbonate, etc. The complexes have a number of uses, including the treatment of elevated blood glucose and related disorders, treatment of proliferative disorders, etc.

DESCRIPTION OF THE SPECIFIC EMBODIMENTS

Figure 1:
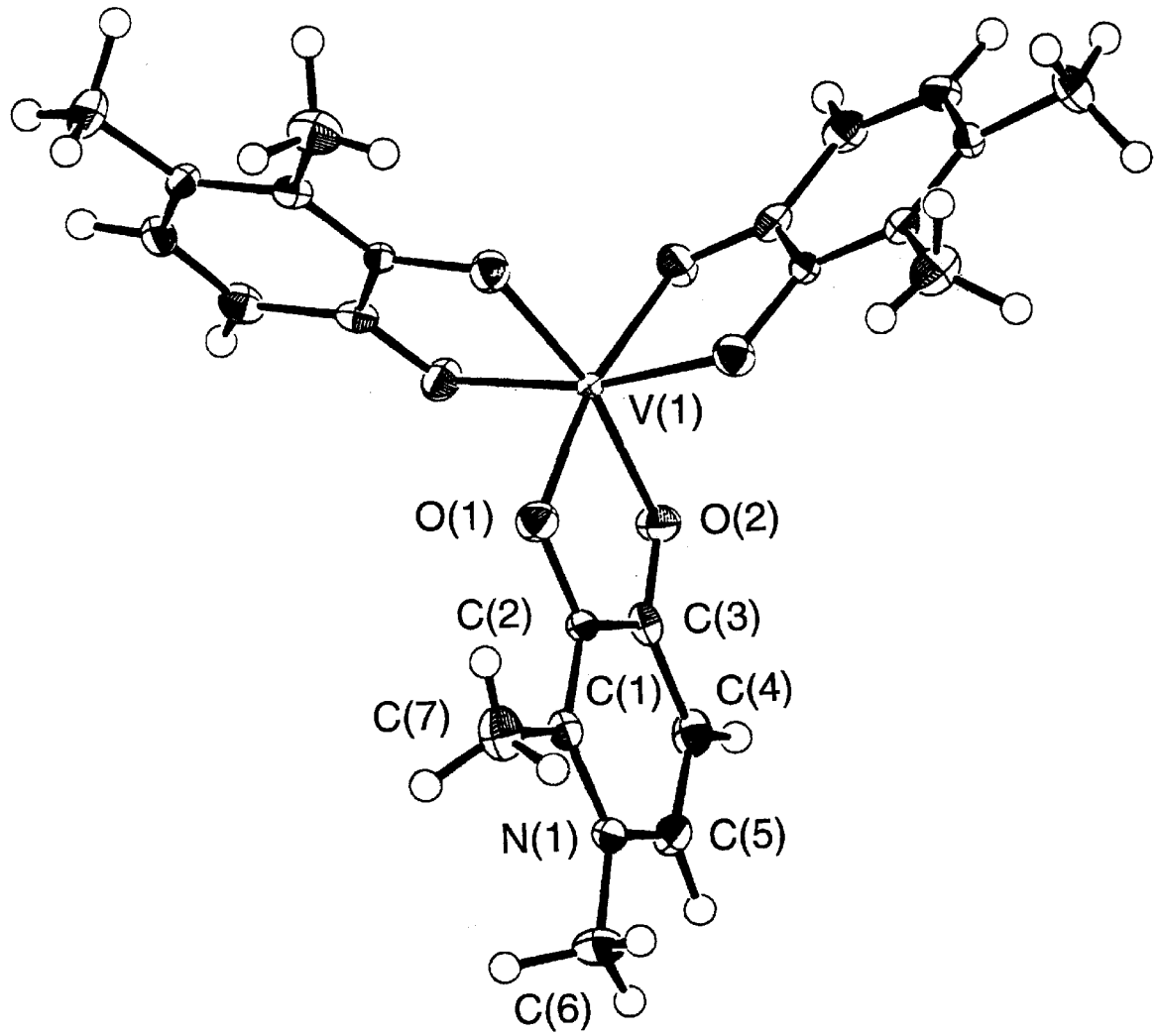
FIG. 1 is an Oakridge Thermal Ellipsoid representation of the crystallographically determined structure of tris(3-hydroxy-$O^3\kappa$-1,2-dimethyl-pyrid-4-onato-$O^4\kappa$)vanadium (III) dodecahydrate.
Figure 2A:
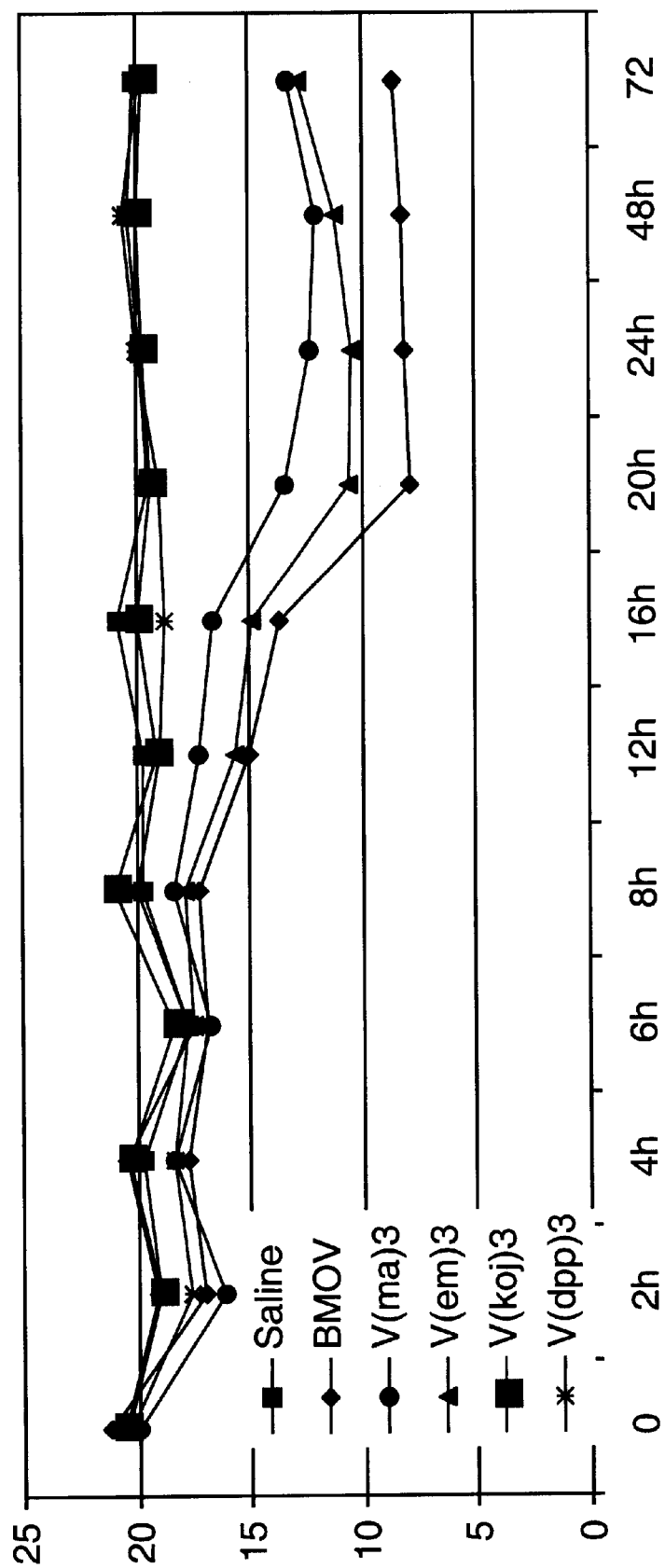
FIG. 2A shows a comparison of the glucose lowering ability of vanadium complexes in diabetic rats over a time course.
Figure 2B:
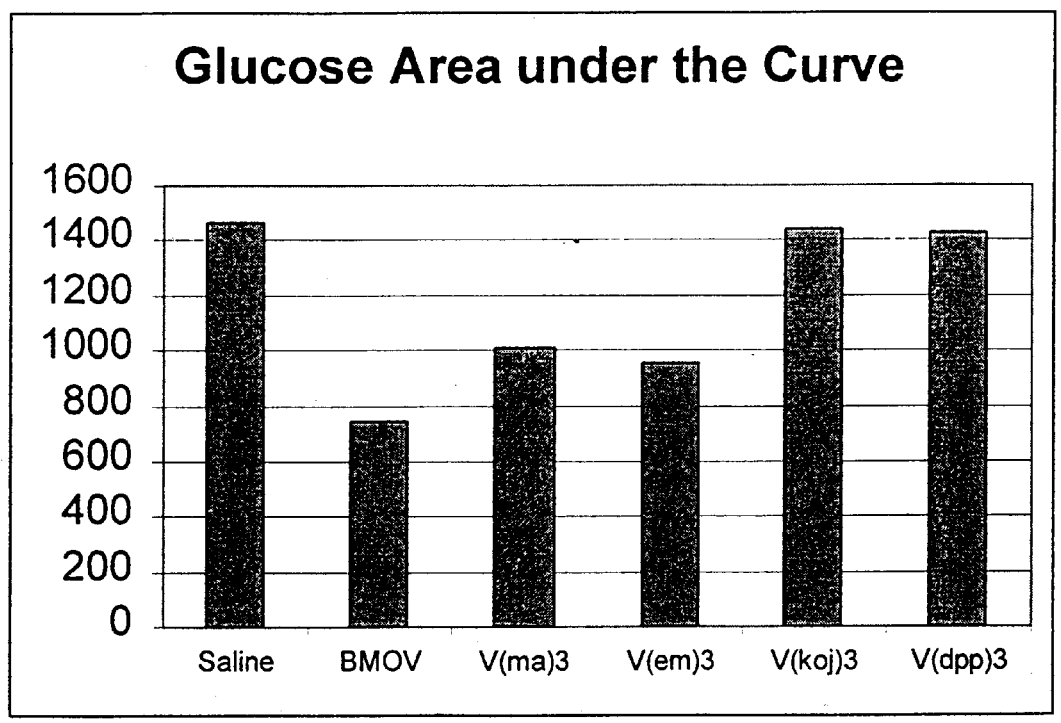
FIG. 2B provides a summary of the comparison, showing the area under the curve (AUC).

Organic complexes of vanadium(III) are provided, with the general structure $VL_3$, where L is a monoprotic bidentate ligand that forms a five-membered, unsaturated vanadium containing ring, having vanadium coordinating oxygen or sulfur ring heteroatoms, and where the vanadium containing ring is fused to a six-membered heterocyclic ring.

In a preferred embodiment, the ligands are hydroxy-4-pyrones or hydroxypyridin-4-ones, and the complexes have the structure:

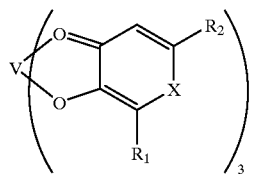

where V is vanadium in the (3+) oxidation state; X is O, S or $NR_3$; and $R_1$, $R_2$ and $R_3$ are, independently, H or a substituent selected from $C_1$ to $C_{20}$ alkyl, usually lower alkyls; $C_1$ to $C_{20}$ alcohols, usually lower alcohols; $C_3$ to $C_{12}$ cycloalkyl; $C_3$ to $C_{12}$ cycloalcohols, $C_6$ to $C_{24}$ aralkyls, $C_6$ to $C_{24}$ arylalcohols; $C_2$ to $C_{16}$ alkyl ethers, thioethers, epoxides, ketones, amines, amides or esters; $C_7$ to $C_{27}$ araalkyl ethers; thioethers, epoxides, ketones, amines, amides or esters.

The complex may also be provided in the form of a hydrate, $VL_3\cdot(H_2O)_n$, where $VL_3$ is as defined above, and n is from 0 to 20, usually from not more than 16. In one embodiment of the invention, n is 12. The complex may also be provided in the form of $VL_3\cdot(Z)_m$, where $VL_3$ is as defined above, Z is an acid, usually a physiologically acceptable acid, e.g. HCl, ascorbic acid, acetic acid, etc., and m is a whole number from 0 to 3.

The complexes have a number of uses, including the treatment of elevated blood glucose and related disorders, treatment of proliferative disorders, etc.; as a catalyst for oxidation or reduction reactions; as a dye; etc. Methods of use are also provided herein.

Oranic $V^{III}$ Complexes

The ligands, or chelants, of the invention have a preferred structure as follows:

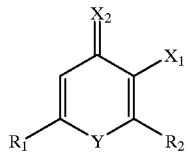

wherein $X_1$ is O; $X_2$ is O;

$R_2$ is hydrogen or is selected from a $C_1$ to $C_4$ lower alkyl group or a $C_1$ hydroxyalkyl group, preferably hydroxymethyl radical, and most preferably hydrogen;

$R_1$ is hydrogen or is selected from a $C_1$ to $C_4$ lower alkyl group or a $C_1$ hydroxyalkyl group, preferably ethyl or methyl, most preferably methyl;

Y is O or is selected from $NR_3$, wherein $R_3$ is hydrogen or is selected from $C_1$ to $C_8$ alkyl radicals or $C_7$ to $C_2$ aralkyl radicals.

The ligands described herein are either commercially available, preparable by conventional disclosed synthetic methods, or are preparable using conventional organic synthetic methods known or available to those skilled in the art of organic synthesis. For example, the commercially available 3-hydroxy-4-pyrones maltol (3-hydroxy-2-methyl-4H-pyran-4-one), ethylmaltol (3-hydroxy-2-ethyl4H-pyran4-one) and kojic acid (5-hydroxy-2-hydroxymethyl-4H-pyran-4-one) serve as suitable starting materials for ligand modifications.

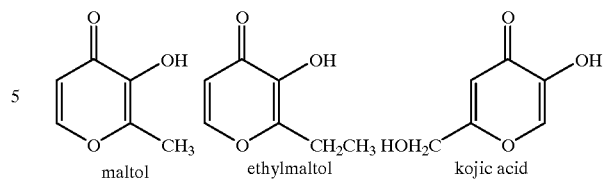

maltol    ethylmaltol    kojic acid

The 3-hydroxypyrid-4-ones are either commercially available (3-hydroxy-2,3-dimethyl-4H-pyrid-4-one) or are readily synthesized from the condensation of the 3-hydroxy-4-pyrone with a primary amine with the formula $R_3NH_2$.

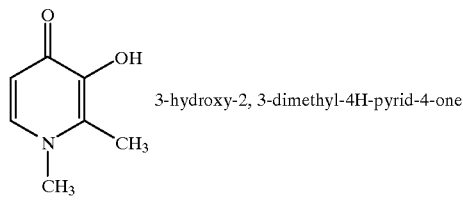

3-hydroxy-2, 3-dimethyl-4H-pyrid-4-one

In general the complexes are prepared using a source of V(III), typically using the reduction of oxovanadium(IV) sulphate to vanadium(III) by hydrosulphite in aqueous solution, combined with the ligands detailed above to form complexes. Complex formation may be effected by conventional metallation or transmetallation techniques, e.g. by mixture in solution of a soluble vanadium salt with the chelant or a salt or weaker complex thereof.

The complexes of the invention are usually neutral in charge, and are stable. As used herein, the term "stable" is intended to refer to compounds or complexes that are substantially stable with respect to retention of oxidation state, charge and ligand under ordinary conditions, e.g. at room temperature when present as a crystalline solid.

The complexes can be isolated by conventional methods, including crystallization, and the like, and may be provided in an isolated form as a solid or as a solution in water or other common solvents, e.g. ethanol, DMSO, etc. or in a composition with other agents, e.g. physiologically acceptable carriers, vanadium complexes of the same or a different oxidation state, e.g. V(IV) complexes, pharmaceutical compositions with other active ingredients, etc.

Pharmaceutical Formulations

The vanadium(III) complexes of the invention, herein termed "$V^{III}$ complexes" can be given by various conventional administration routes, e.g. oral, rectal, intravenous, subcutaneous, intraperitoneal, transdermal, etc. However oral administration is preferred.

Formulations of the $V^{III}$ complexes are administered to a host affected by hyperglycemia, particularly non-insulin dependent diabetes mellitus (NIDDM); by related disorders, which may include obesity, hypertension, hypercholesterolemia, hypertriglyceridemia, etc.; by proliferation disorders, e.g. cancer, restenosis, rheumatoid arthritis; or by loss of bone density, e.g. osteoporosis. The compounds of the present invention are administered at a dosage that reduces blood sugar, blood pressure, etc., while minimizing any side-effects. It is contemplated that the composition will be obtained and used under the guidance of a physician for in vivo use. Such guidance may include non-pharmacological disease management, e.g. diet, exercise, etc.

Various methods for administration may be employed. The formulation may be given orally, by inhalation, or may be injected, e.g. intravascular, intratumor, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously.

The $V^{III}$ complexes of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the $V^{III}$ complexes can be achieved in various ways, including oral, buccal, rectal, parenteral, intraperitoneal, intradermal, transdermal, intracheal, etc., administration. The complexes may be systemic after administration or may be localized by the use of an implant that acts to retain the active dose at the site of implantation.

In pharmaceutical dosage forms, the $V^{III}$ complexes may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the $V^{III}$ complexes can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The $V^{III}$ complexes can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The $V^{III}$ complexes can be utilized in aerosol formulation to be administered via inhalation. The compounds of the present invention can be formulated into pressurized acceptable propellants such as dichlorodifluoromethane, propane, nitrogen and the like.

Furthermore, the $V^{III}$ complexes can be made into suppositories by mixing with a variety of bases such as emulsifying bases or water-soluble bases. The $V^{III}$ complexes of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline. or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing $V^{III}$ complexes is placed in proximity to the site of action, so that the local concentration of active agent is increased relative to the rest of the body.

The term "unit dosage form," as used herein, refers to physically discrete units suitable as unitary dosages for human and animal subjects, each unit containing a predetermined quantity of $V^{III}$ complexes of the present invention calculated in an amount sufficient to produce the desired effect in association with a pharmaceutically acceptable diluent, carrier or vehicle. The specifications for the novel unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compositions of the invention may also contain other therapeutically active agents, e.g. antidiabetic, antihypertensive and appetite suppressing agents, e.g. aldose reductase inhibitors, sulfonylureas, $MgCl_2$, chromium picolinate, chemotherapeutic agents, etc. Of particular interest are combinations with other agents capable of additive or synergistic effect in achieving a therapeutic result, e.g. where a different or complementary pathway is affected by each of the active agents.

For example, in the treatment of hyperglycemia, insulin may be administered during the course of treatment with the subject $V^{III}$ complexes. Various compositions and formulations of insulin are known in the art, including recombinant human insulin, bovine or porcine insulin, etc., as a protamine zinc suspension, zinc suspension, etc., formulated for intravenous injection, subcutaneous injection, aerosol administration, etc. Standard adult doses for insulin range from about 5 to 20, and as much as about 80 USP units per day.

The combined used of $V^{III}$ complexes and other agents has the advantages that the required dosages for the individual drugs may be lower, and the onset and duration of effect of the different drugs complementary. In the combined therapy, the different active agents can be delivered together or separately, and simultaneously or at different times within the day. Moreover the compounds may be administered by any convenient and effective route, e.g. by injection, orally, rectally or transdermally. Preferably, where the agents are orally active, administration will be orally and the different agents will be administered substantially simultaneously, preferably as a composition containing both agents. Where one of the agents is insulin, which is not orally active, the agents will generally be separately formulated.

Dosages

Depending on the patient and condition being treated and on the administration route, the $V^{III}$ complexes will generally be administered in dosages of 0.1 mg to 500 mg V/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. As a result, the preferred range for rats is 0.1 to 300 mg V/kg/day while for man it may be 0.007 to 2.0 mg V/kg/day.

A typical dosage may be one tablet taken from two to three times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific complexes are more potent than others. Preferred dosages for a given complex are readily determinable by those of skill in the art by a variety of means. A preferred means is to measure the physiological potency of a given compound.

Methods of Use

Patients suitable for the treatment with the subject $V^{III}$ complexes include those with diabetes mellitus, a mammalian condition in which the amount of glucose in the blood plasma is abnormally high. This condition can be life-threatening, and high glucose levels in the blood plasma (hyperglycemia) can lead to a number of chronic diabetes syndromes, for example, atherosclerosis, microangiopathy, kidney disorders, renal failure, cardiac disease, diabetic retinopathy and other ocular disorders including blindness. In diabetics, insulin is not produced in sufficient quantities, or the body becomes tolerant to insulin and requires more than normal amounts to produce the necessary effect.

Patients are generally categorized as diabetic or hyperglycemic by measuring the level of glucose in the blood, either directly or by monitoring the level of glycosylated hemoglobin. Treatment is recommended where fasting glucose levels are greater 140 mg/dl, where bedtime glucose is greater than 160 mg/dl, or where $HbA_{1c}$ is greater than 8%. The level of reduction that is desirable depends on the condition of the patient, and the blood glucose levels at the start of treatment, but generally about a 10 to 40% reduction is blood glucose is desirable, usually about a 25 to 35% reduction.

| Glycemic control for people with diabetes | | | |
|---|---|---|---|
| Biochemical index | Fasting glucose | Bedtime glucose (mg/dl) | $HbA_{1c}$ (%) |
| Nondiabetic | <115 | <120 | <6 |
| Goal | 80–120 | 100–140 | <7 |
| Action suggested | >140 | >160 | >8 |

Insulin resistance is an essential feature of a great variety of clinical disorders, such as diabetes mellitus, obesity and certain types of hypertension. Individuals with non-insulin dependent diabetes present with insulin resistance in peripheral tissues. They have a subnormal glucose utilization in skeletal muscle, where glucose transport across the cell membrane of skeletal muscle is the rate limiting step in glucose metabolism. It is possible that a defect exists in insulin-dependent glucose transport in skeletal muscle in diabetic states, where decreased levels of the glucose transporter 4 protein (GLUT4) have been observed. In adipose and muscle cells, insulin stimulates a rapid and dramatic increase in glucose uptake, primarily by promoting the redistribution of the GLUT4 glucose transporter from its intracellular storage site to the plasma membrane. Impaired glucose tolerance (IGT) is associated with a normal fasting blood glucose but an elevated postprandial blood sugar between 7.8 and 11 mmol/L (140 and 199 mg/dL). Some patients with IGT are hyperinsulinimic, and 30 percent progress to NIDDM.

The subject complexes may be administered to obese patients for purposes of appetite suppression. Human obesity is a widespread and serious disorder, affecting a high percentage of the adult population in developed countries. In spite of an association with heart disease, type II diabetes, cancer, and other conditions, few persons are able to permanently achieve significant weight loss. Patients may use various criteria for determining obesity. Conveniently, a body mass index (BMI) is calculated, where a person having a BMI of greater than 25 is overweight and may considered for treatment with the subject vanadium complex formulations.

Hypertension and diabetes mellitus are interrelated diseases, which, if untreated, strongly predispose to atherosclerotic cardiovascular disease. Lifestyle and genetic factors are important in the genesis of both conditions. An estimated 3 million Americans have both diabetes and hypertension. Hypertension is approximately twice as common in persons with diabetes as in those without. The prevalence of hypertension and type II diabetes, or non-insulin-dependent diabetes mellitus (NIDDM), increases with age.

Hypertension should not be diagnosed on the basis of a single measurement. Initial elevated readings should be confirmed on at least two subsequent visits over 1 week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

Alterations in circulating lipids are also commonly associated with diabetes and hyperglycemic. Persons with type II diabetes and impaired glucose tolerance experience twice the incidence of hypertriglyceridemia and low high density lipoprotein (HDL) cholesterol of persons who do not have diabetes. These changes are thought to be related to insulin resistance and hyperinsulinemia. Low density lipoprotein (LDL) cholesterol in diabetes is more prone to glycation and oxidation. These biochemical changes increase the atherogenicity and decrease the metabolism of LDL cholesterol.

The subject complexes may also be used in the treatment of proliferative disorders, e.g. cancer, restenosis, rheumatoid arthritis, and the like. Cancer cells that may be treated with the subject complexes include carcinomas, e.g. skin, prostate, breast, adenocarcinoma; lung; mesotheliomas; neuroblastomas; lymphomas, leukemias, sarcomas; melanomas; etc.

For use in cancer treatment, the complexes may be formulated with other pharmaceutically active antimetastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

The complexes may also be administered for the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

The subject complexes may also be utilized in the treatment for loss of bone density. Patients suffering from loss of bone density include postmenopausal women, patients who have undergone hysterectomy, senile ostoeporosis, patients who are undergoing or have undergone long term administration of corticosteroids, patients suffering from Cushing's syndrome, and patients having gonadal dysgenesis. Methods for the inhibition of bone loss include both therapeutic and prophylactic treatment, i.e. for an individual who is suffering from bone loss as well as one who is at risk of future bone loss.

Fracture rate as a consequence of osteoporosis is inversely correlated with bone mineral density. However, changes in bone density occur only slowly, and are meaningful only after several months or years. One can determine whether there is a therapeutic effect in shorter time periods by measuring various quickly responding biochemical parameters that reflect changes in skeletal metabolism. A baseline examination of a patient may include quantitative measurements of urinary calcium, creatine, hydroxyproline, and pyridinol cross-links. Blood samples are measured for osteocalcin and bone-specific alkaline phosphatase. All of these biochemical markers are associated with bone resorption and are known to respond to agents effective in the treatment of postmenopausal osteoporosis. In longer term studies, measuring the change in bone mineral density may also be performed. The bone mineral density is measured by either single photon or dual energy X-ray absorptiometry (DEXA) of the femur or tibia.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods, ligands, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

EXPERIMENTAL

The present invention will be further illustrated with reference to the following examples which aid in the understanding of the present invention, but which are not to be construed as limitations thereof. All temperatures are absolute, expressed in degrees Kelvin. The reagent chemicals employed herein were obtained from commercial sources, e.g. the Aldrich Chemical Co., St. Louis, Mo. Syntheses were in part derived from Dilli et al. (1976) *Aust. J. Chem* 29:2389–93, which describes the convenient synthesis of V(III) acetylacetonates.

EXAMPLE 1

Tris(3-hydroxy-$O^3\kappa$-1,2-dimethyl-pyrid-4-onato-$O^4\kappa$)vanadium(III) dodecahydrate

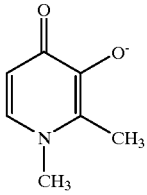

Pale blue bis(3-hydroxy-O3κ-1,2-dimethyl-pyrid-4-onato-O4κ) oxovanadium(IV) (1.029) was suspended in a solution of 0.417 g of 3-hydroxy-1,2-dimethyl-pyrid-4-one in 30 mL $H_2O$ at 333 K with stirring under Ar. Reaction with sodium hydrosulphite (1.933 g) in 5 mL $H_2O$ for 1 hour, followed by cooling to RT results in a yellow hygroscopic precipitate which was collected on a medium porosity frit. Crystals suitable for X-ray diffraction were grown from a saturated $H_2O$ solution.

EXAMPLE 2

Tris(3-hydroxy-$O^3\kappa$-2-methyl-4H-pyran-4-onato-$O^4\kappa$)vanadium(III)

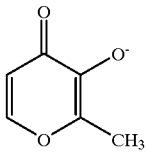

Oxovanadium(IV) sulphate trihydrate (10.83 g) and 3-hydroxy-2-methyl-4H-pyran-4-one (18.81 g) were dissolved at 333 K in 0.3 L of $H_2O$ under a positive flow of Ar. Reduction with sodium hydrosulphite (25.00 g) yields a dark red microcrystalline solid (13.76 g) which was collected by filtration, washed with water, air dried and then dried in vacuo.

EXAMPLE 3

Tris(3-hydroxy-$O^3\kappa$-2-ethyl-4H-pyran-4-onato-$O^4\kappa$)vanadium(III):

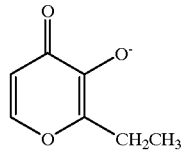

Oxovanadium(IV) sulphate trihyd rate (10.83 g) and 3-hydroxy-2-ethyl-4H-pyran-4-one (20.60 g) were dissolved at 333 K in 0.3 L of $H_2O$ under Ar. Reduction with sodium hydrosulphite (25.00 g) yields a dark red microcrystalline solid (20.44 g) which was collected by filtration, washed with water and dried in vacuo.

EXAMPLE 4

Tris(5-hydroxy-$O^5\kappa$-3-hydroxymethyl-4H-pyran-4-onato-$O^4\kappa$)vanadium(III):

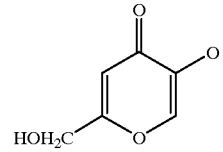

Oxovanadium(IV) sulphate trihydrate (2.13 g) and 5-hydroxy-3-hydroxymethyl-4H-pyran-4-one (4.26 g) were dissolved in 50 mL $H_2O$ at 333 K. Reduction with sodium hydrosulphite (5.35 g) yields an orange powder (3.60 g) which was collected by filtration on a medium porosity frit, washed with water, air dried and subsequently dried in vacuo.

EXAMPLE 5

Tris(3-hydroxy-$O^3\kappa$-2-methyl-4H-pyran-4-one-$O^4\kappa$) vanadyl(III) trihydrochloride

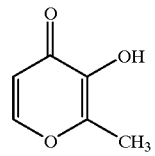

Solid red V(maltol)$_3$ (33 mg) was allowed to equilibrate for two days at RT, in a closed two compartment system with conc. HCl yielding, upon drying in vacuo, a yellow solid (37 mg).

Table 1 below provides physical data of the complexes prepared in the preceding examples.

TABLE 1

| | Selected infra-red absorption data (cm$^{-1}$, KBr disk) |
|---|---|
| example 1 | 3616-3118, 1608, 1550, 1502, 1514, 1463, 1452, 1342, 1280, 1259, 1172, 1122, 1066, 1031, 916, 826, 768, 705, 628 |
| example 2 | 3070, 2918, 1608, 1572, 1506, 1466, 1384, 1366, 1295, 1270, 1244, 1201, 1090, 1040, 992, 925, 848, 766, 722, 626 |
| example 3 | 3076, 2973, 2937, 2888, 1601, 1569, 1503, 1470, 1332, 1261, 1239, 1188, 1103, 1065, 1042, 990, 942, 843, 763, 718 |
| example 4 | 3560-3117, 2967, 2899, 2843, 1611, 1566, 1518, 1471, 1264, 1240, 1195, 1151, 1077, 1024, 987, 943, 916, 867, 798, 759, 693, 644, 568 |
| example 5 | 3560-2630, 1624, 1477, 1364, 1266, 1201, 1081, 1033, 932, 849, 730 |

| | Elemental analysis data for examples 2 and 4 | | | |
|---|---|---|---|---|
| | % C experimental | % H experimental | % C calculated | % H calculated |
| example 2 | 50.52 | 3.56 | 50.72 | 3.55 |
| example 4 | 43.26 | 3.46 | 43.13 | 3.62 |

| Selected mass spectral data (+LSIMS) for examples 2, 3 and 4. | | |
|---|---|---|
| | $VL_2^+$ | $V_2L_5^+$ |
| example 2 | 301 | 727 |
| example 3 | 329 | 797 |
| example 4 | 333 | 807 |

| Selected X-ray crystallographic data for example 1 (a representation is shown as FIG. 1) |
|---|
| V(1)-O(1) length: 2.0067(14)Å |
| V(1)-O(2) length: 2.0354(14)Å |
| O(1)-V(1)-O(2) angle: 80.57(6)° |

| Proton NMR chemical shift data for example 5 at 200 MHz (ppm) | |
|---|---|
| $H_a$ (HHH, HHD, HDD) | −6.75, −8.15, −8.97 |
| $H_b$ | 2.19 |
| $H_c$ | 7.81 |
| $H_d$ | 6.32 |

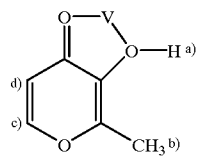

| Treatment | Group size |
|---|---|
| diabetic, saline | n = 5 |
| BMOV | n = 5 |
| tris(maltolato)vanadium(III), $(V(ma)_3)$ | n = 5 |
| tris(ethylmaltolato)vanadium(III), $(V(ema)_3)$ | n = 5 |
| tris(kojic acid)vanadium(III), $(V(koj)_3)$ | n = 5 |
| (diethylpyridinone)vanadium(III), $V(dpp)_3$ | n = 5 |

All the compounds were administered in saline. Drugs were administered by intraperitoneal injection at a volume of 10 ml/kg. The dose of administration was 0.1 mmol/kg. The V(III) compounds were prepared, and sparged of oxygen under argon. The control group received an equivalent volume of saline alone. Animals were not fasted prior to drug administration.

50 μl of blood was collected for glucose analysis immediately prior to drug administration and at 2, 4, 6, 8, 12, 16, 20, 24, 48 and 72 hours following drug administration. Blood was collected from the tail into heparinized capillary tubes and centrifuged at 10,000 g×15 minutes. The plasma was analyzed immediately for glucose levels using Boehringer Mannheim kits (glucose oxidase method). At all time points animals were observed for signs of toxicity (diarrhea, etc.) The results are shown in Table 2.

These results demonstrate that these organic complexes of vanadium(III) are active as glucose-lowering agents.

TABLE 2

| Time blood drawn Test compound | Pre treatment | 2 h | 4 h | 6 h | 8 h | 12 h | 16 h | 20 h | 24 h | 48 h | 72 | Area under Curve mmol/L/h |
|---|---|---|---|---|---|---|---|---|---|---|---|---|
| | | | | Blood Glucose levels in mmol/L | | | | | | | | |
| Saline control | 20.48 | 19.01 | 19.71 | 17.72 | 19.68 | 19.68 | 20.78 | 19.41 | 19.78 | 20.34 | 20.06 | 1460.93 |
| BMOV | 21.15 | 17.02 | 17.78 | 16.92 | 17.25 | 14.99 | 13.68 | 7.94 | 8.16 | 8.19 | 8.61 | 741.28 |
| $V(ma)_3$ | 19.91 | 16.16 | 18.40 | 16.78 | 18.32 | 17.22 | 16.57 | 13.39 | 12.34 | 12.07 | 13.24 | 1004.75 |
| $V(em)_3$ | 20.58 | 19.63 | 20.42 | 17.43 | 17.91 | 15.66 | 14.85 | 10.63 | 10.47 | 11.17 | 12.82 | 952.38 |
| $V(koj)_3$ | 20.55 | 19.00 | 20.31 | 18.38 | 20.92 | 19.04 | 19.98 | 19.33 | 19.73 | 19.99 | 19.69 | 1442.40 |
| $V(dpp)_3$ | 20.27 | 17.57 | 18.33 | 17.69 | 19.95 | 18.97 | 18.78 | 18.99 | 19.92 | 20.6 | 19.83 | 1428.23 |

EXAMPLE 6

Plasma Glucose Lowering Effects

The plasma glucose lowering effect for a group of organic vanadium(III) compounds was tested in STZ-diabetic rats following a single intraperitoneal injection, compared to bis(maltolato)oxovanadium(IV) (BMOV).

Methods

Thirty male Wistar rats weighing 190–220 g were obtained, and acclimated for a period of 7–14 days. Animals were made diabetic with a single intravenous injection of streptozocin at 60 mg/kg in 0.9% NaCl (1 ml/kg volume) under light halothane anaesthesia. On day 3 post-STZ the diabetic state was confirmed with blood glucometer (Ames glucometer and Glucostix) readings. Blood glucose levels of greater than 13 mM were taken as diabetic.

Day 7 post STZ animals were divided randomly into 6 groups:

What is claimed is:

1. An organic vanadium complex, having the structure $VL_3$, where V is vanadium in the (+3) oxidation state, and L is a bidentate monoprotic ligand that forms a five-membered, unsaturated vanadium containing ring, and where the vanadium containing ring is fused to a six-membered heterocyclic ring having the structure:

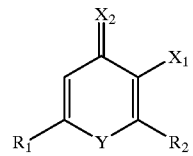

wherein $X_1$ and $X_2$ are, independently, O or S and are vanadium coordinating;

R₂ is hydrogen or is selected from a $C_1$ to $C_4$ lower alkyl group or a $C_1$ hydroxyalkyl group;

R₁ is hydrogen or is selected from a $C_1$ to $C_4$ lower alkyl group or a $C_1$ hydroxyalkyl group;

Y is O or NR₃, wherein R₃ is hydrogen or is selected from $C_1$ to $C_8$ alkyl radicals or $C_7$ to $C_{12}$ aralkyl radicals.

2. A method of treatment for a hyperglycemic related disorder selected from the group consisting of non-insulin dependent diabetes mellitus, obesity, hypertension, hypercholesterolemia, and hypertriglyceridemia, the method comprising:

administering to a patient suffering from said hyperglycemic related disorder an effective dose of the an organic vanadium complex having the structure VL₃, where V is vanadium in the (+3) oxidation state, and L is a bidentate monoprotic ligand that forms a five-membered, unsaturated vanadium containing ring, and where the vanadium containing ring is fused to a six-membered heterocyclic ring having the structure:

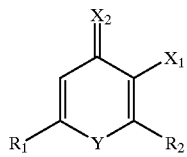

wherein X₁ and X₂ are, independently, O or S and are vanadium coordinating;

R₂ is hydrogen or is selected from a $C_1$ to $C_4$ lower alkyl group or a $C_1$ hydroxyalkyl group;

R₁ is hydrogen or is selected from a $C_1$ to $C_4$ lower alkyl group or a $C_1$ hydroxyalkyl group;

Y is O or NR₃, wherein R₃ is hydrogen or is selected from $C_1$ to $C_8$ alkyl radicals or $C_7$ to $C_{12}$ aralkyl radicals; and a physiologically acceptable carrier;

wherein said hyperglycemic related disorder is inhibited.

3. The method according to claim 2, wherein said hyperglycemic related disorder is non-insulin dependent diabetes mellitus.

4. The method according to claim 2, wherein said hyperglycemic related disorder is obesity.

5. The method according to claim 2, wherein said hyperglycemic related disorder is hypertension.

6. The method according to claim 2, wherein said hyperglycemic related disorder is hypercholesterolemia.

7. The method according to claim 2, wherein said hyperglycemic related disorder is hypertriglyceridemia.

8. The organic vanadium complex of claim 7, wherein L is a hydroxypyrone.

9. The organic vanadium complex of claim 1, wherein L is a hydroxypyridone.

10. The organic vanadium complex of claim 7, wherein L is selected from the group consisting of 3-hydroxy-2-methyl-4H-pyran-4-one, 3-hydroxy-2-ethyl-4H-pyran-4-one, 5-hydroxy-2-hydroxymethyl-4H-pyran-4-one, and 3-hydroxy-2,3-dimethyl-4H-pyrid-4-one.

11. The organic vanadium complex of claim 1, wherein X¹ and X₂ are O; Y is O; R₁ is hydrogen and R₂ is a $C_1$ to $C_2$ alkyl radical or $C_1$ hydroxy hydroxyalkyl group.

12. The organic vanadium complex of claim 1, wherein X₁ and X₂ are O; Y is NR₃ wherein R₁ is a C1 to C2 alkyl radical; R₂ is hydrogen; and R₃ is hydrogen or is selected from methyl, and ethyl.

13. The method of claim 2, wherein L is a hydroxypyrone or hydroxypyridone.

14. The method according to claim 13, wherein L is selected from the group consisting of 3-hydroxy-2-methyl-4H-pyrah-4-one, 3-hydroxy-2-ethyl-4H-pyran-4-one, 5-hydroxy-2-hydroxymethyl-4H-pyran-4-one, and 3-hydroxy-2,3-dimethyl-4H-pyrid-4-one.

15. The method of claim 2 further comprising:

administering a second physiologically active agent effective in inhibiting said hyperglycemic related disorder.

16. The method of claim 2, wherein said administering step comprises oral administration.

17. A pharmaceutical composition, comprising an organic vanadium complex having the structure VL₃, where V is vanadium in the (+3) oxidation state, and L is a bidentate monoprotic ligand that forms a five-membered, unsaturated vanadium containing ring, and where the vanadium containing ring is fused to a six-membered heterocyclic ring having the structure:

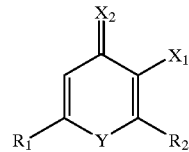

wherein X₁ and X₂ are, independently, O or S and are vanadium coordinating;

R₂ is hydrogen or is selected from a $C_1$ to $C_4$ lower alkyl group or a $C_1$ hydroxyalkyl group;

R₁ is hydrogen or is selected from a $C_1$ to $C_4$ lower alkyl group or a $C_1$ hydroxyalkyl group;

Y is O or NR₃, wherein R₃ is hydrogen or is selected from $C_1$ to $C_8$ alkyl radicals or $C_7$ to $C_{12}$ aralkyl radicals.

18. The pharmaceutical composition of claim 17, wherein L is a hydroxypyridone.

19. The pharmaceutical composition of claim 17, wherein L is selected from the group consisting of 3-hydroxy-2-methyl-4H-pyran-4-one, 3-hydroxy-2-ethyl-4H-pyran-4-one, 5-hydroxy-2-hydroxymethyl-4H-pyran-4-one, and 3-hydroxy-2,3-dimethyl-4H-pyrid-4-one.

20. The pharmaceutical composition of claim 19, wherein L is a hydroxypyrone.

* * * * *